United States Patent
Fievez

(10) Patent No.: US 8,225,642 B2
(45) Date of Patent: Jul. 24, 2012

(54) APPARATUS AND METHOD FOR CONDITION MONITORING OF A COMPONENT OR STRUCTURE

(75) Inventor: Jonathan Fievez, Melville (AU)

(73) Assignee: Structural Monitoring Systems Ltd., Osborne Park (AU)

( * ) Notice: Subject to any disclaimer, the term of this patent is extended or adjusted under 35 U.S.C. 154(b) by 395 days.

(21) Appl. No.: 12/517,720

(22) PCT Filed: Nov. 27, 2007

(86) PCT No.: PCT/AU2007/001820
§ 371 (c)(1),
(2), (4) Date: Feb. 9, 2010

(87) PCT Pub. No.: WO2008/067586
PCT Pub. Date: Jun. 12, 2008

(65) Prior Publication Data
US 2010/0139370 A1 Jun. 10, 2010

(30) Foreign Application Priority Data
Dec. 5, 2006 (AU) .............................. 2006906797

(51) Int. Cl.
*G01N 15/08* (2006.01)
(52) U.S. Cl. .......................................................... 73/38
(58) Field of Classification Search ................ 73/40, 46, 73/47, 49.8, 38
See application file for complete search history.

(56) References Cited

U.S. PATENT DOCUMENTS

| | | | | |
|---|---|---|---|---|
| 4,104,906 A | * | 8/1978 | Oertle | 73/104 |
| 4,135,386 A | | 1/1979 | Peterson et al. | |
| 4,145,915 A | * | 3/1979 | Oertle et al. | 73/37 |
| 4,198,853 A | * | 4/1980 | Graham et al. | 73/38 |
| 4,444,041 A | * | 4/1984 | Zison | 73/19.04 |
| 4,776,206 A | * | 10/1988 | Armstrong et al. | 73/40 |
| 4,953,388 A | * | 9/1990 | Barada | 73/37.5 |
| 4,979,390 A | * | 12/1990 | Schupack et al. | 73/38 |
| 5,014,544 A | * | 5/1991 | West | 73/40.7 |
| 5,404,747 A | * | 4/1995 | Johnston et al. | 73/40 |
| 5,544,520 A | * | 8/1996 | Graf et al. | 73/38 |
| 5,770,794 A | * | 6/1998 | Davey | 73/37 |

(Continued)

FOREIGN PATENT DOCUMENTS
SU 530214 12/1976

*Primary Examiner* — John Fitzgerald
(74) *Attorney, Agent, or Firm* — Meyertons, Hood, Kivlin, Kowert & Goetzel, P.C.; Eric B. Meyertons

(57) ABSTRACT

An apparatus (10) monitors the condition of a component (12) by measuring the conductivity to air flow of a sealed cavity (14) formed on the surface of the component (12). The apparatus (10) comprises an unregulated pressure source (16) that is coupled to the cavity (14) via a fluid flow restriction (17). A measurement system (19) provides a measurement of, or related to, the volumetric air flow through the restriction (17), and calculates a conductivity index CI to air flow of the cavity in accordance with the equation CI=flow/pressure difference. In this equation "flow" is the volumetric flow of air through the flow restriction and "pressure difference" is the difference in pressure across the cavity with reference to atmospheric or ambient pressure. In the event that a crack traverses the cavity and provides a flow path to the atmosphere, the conductivity index CI will be a non-zero value. The higher the conductivity index the larger the crack.

20 Claims, 1 Drawing Sheet

U.S. PATENT DOCUMENTS

| | | | |
|---|---|---|---|
| 5,795,995 A * | 8/1998 | Shimaoka et al. | 73/40 |
| 6,539,776 B2 * | 4/2003 | Davey | 73/37 |
| 6,591,661 B2 | 7/2003 | Davey | |
| 6,598,458 B1 * | 7/2003 | Edwards et al. | 73/19.1 |
| 6,692,970 B2 * | 2/2004 | Butnor et al. | 436/148 |
| 6,715,365 B2 | 4/2004 | Davey | |
| 6,720,882 B2 * | 4/2004 | Davey | 340/611 |
| 7,392,689 B2 * | 7/2008 | Kim et al. | 73/31.02 |
| 7,509,836 B2 * | 3/2009 | Johnson et al. | 73/19.01 |
| 7,568,374 B2 * | 8/2009 | Johnson et al. | 73/19.01 |
| 2006/0213255 A1 * | 9/2006 | Zhu et al. | 73/53.03 |
| 2009/0301234 A1 * | 12/2009 | Risk | 73/864.83 |

* cited by examiner

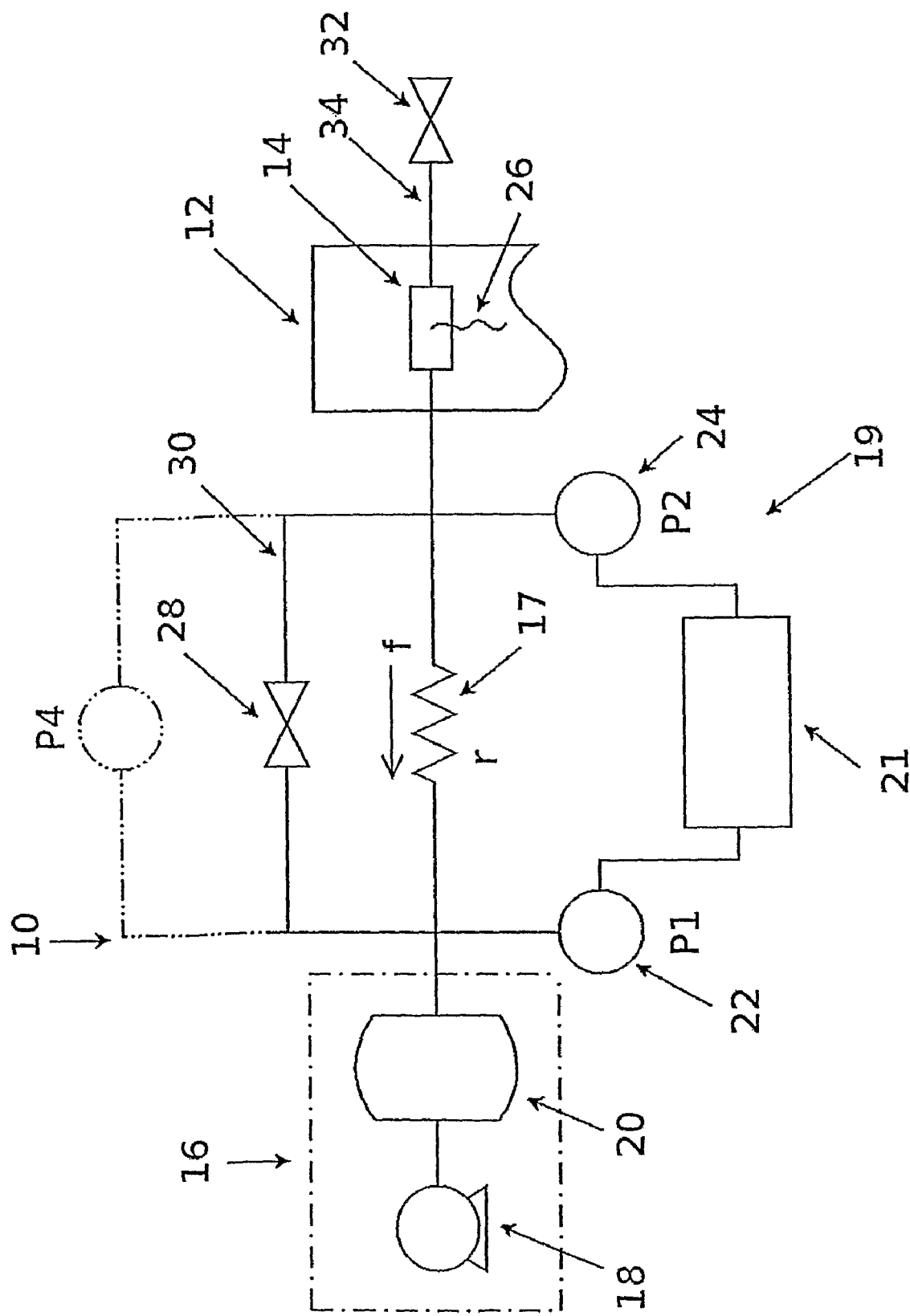

APPARATUS AND METHOD FOR CONDITION MONITORING OF A COMPONENT OR STRUCTURE

FIELD OF THE INVENTION

The present invention relates to an apparatus and method for the condition monitoring of a component or structure.

BACKGROUND OF THE INVENTION

It is known to use a constant relative vacuum source connected via a high fluid flow impedance to a cavity sealed on or in a component or structure to monitor for impending faults. Such systems are for example described in U.S. Pat. No. 6,539,776; U.S. Pat. No. 6,591,661; U.S. Pat. No. 6,715,365 and U.S. Pat. No. 6,720,882 all assigned to the present applicant; and U.S. Pat. No. 5,770,794 (assigned to Tulip Bay Pty Ltd).

In the claims of this application and in the description of the invention, except where the context requires otherwise due to express language or necessary implication, the words "comprise" or variations such as "comprises" or "comprising" are used in an inclusive sense, i.e. to specify the presence of the stated features but not to preclude the presence or addition of further features in various embodiments of the invention.

It is to be understood that any references to any prior art publication in this specification does not constitute an admission that the publication forms a part of the common general knowledge in the art, in Australia or any other country.

SUMMARY OF THE INVENTION

In accordance with one aspect of the present invention there is provided an apparatus for condition monitoring of a component or structure comprising:
 a sealed cavity on or within the component or structure;
 an unregulated pressure source;
 a fluid flow restriction having a flow resistance r and providing fluid communication between the cavity and the source;
 a measurement system for: providing a measurement of, or related to, the volumetric air flow through the flow restriction and, providing an indication of a conductivity index to air flow of the cavity based on the flow resistance r and the measurement of or related to the volumetric air flow.

In accordance with a further aspect of the present invention there is provided an apparatus for measuring the conductivity to air flow of a sealed cavity formed on a surface of a structure or a component where a portion of the surface forms part of an internal surface of the cavity, the apparatus comprising:
 an unregulated pressure source;
 a fluid flow restrictor having a flow resistance r and providing fluid flow communication between the cavity and the pressure source;
  a measurement system for providing a measurement of, or related to, the volumetric air flow through the flow restriction; and, calculating a conductivity index CI to air flow of the cavity in accordance with the equation
 CI=flow/pressure difference
 where "flow" is the volumetric flow of air through the fluid flow restriction measured by the measurement system; and "pressure difference" is the difference in pressure across the cavity with reference to atmospheric or ambient pressure.

According to a further aspect of the present invention there is provided an apparatus for measuring the conductivity to air flow of a crack on a surface of a structure, the surface having applied to it an impervious member forming a sealed cavity that is breached by the crack, the apparatus comprising:
 an unregulated pressure source;
 a fluid flow restrictor having a flow restrictor r and providing fluid communication between the cavity and the pressure source;
 a measurement system for providing a measurement of, or related to, the volumetric air flow through the flow restriction; and, calculating a conductivity index CI of air flow through the crack on the basis of the flow resistance r and the measurement of volumetric air flow.

In one embodiment the measurement system may comprise a first pressure transducer providing a measure of pressure. P1 of the unregulated pressure source; and, a second pressure transducer providing a measure of pressure P2 on a side of the cavity connected with the fluid flow restrictor.

In one embodiment, the apparatus further comprises a continuity valve coupled to an end of the cavity opposite the fluid flow restrictor, the continuity valve having a ON state in which the valve is open and vents the cavity to atmospheric pressure, and an OFF state in which the continuity valve is shut.

The apparatus may further comprise a bypass valve connected in parallel across the fluid flow restrictor to provide direct fluid communication between the unregulated pressure source and the sealed cavity when the bypass valve is in an ON state.

The apparatus may further comprise an ambient pressure sensor or transducer for providing a measure of ambient pressure P3 and the measurement system includes the measure of ambient pressure in the calculation of the conductivity index. Alternatively a standard or fixed ambient pressure may be provided to the measurement system for calculation of the conductivity index.

A further aspect of the invention provides a method of condition monitoring of a component or a structure comprising:
 forming a substantially sealed cavity on or in the component or structure;
 connecting an unregulated pressure source via a fluid flow restriction to the cavity, where the restriction has a flow resistance r;
 providing an indication of air flow into the cavity based on a measured volumetric air flow through the restriction and a measured pressure difference across the cavity.

BRIEF DESCRIPTION OF THE DRAWING

An embodiment of the present invention will now be described by way of example only with reference to the accompanying drawing.

DETAILED DESCRIPTION OF PREFERRED EMBODIMENT

FIG. 1 illustrates an embodiment of an apparatus 10 for monitoring the condition of a component or structure 12. The apparatus monitors the condition of the component or structure 12 by measuring the conductivity to air flow of a sealed cavity 14 formed on the surface of the structure 12. The precise form of the cavity 14 is not critical to embodiments of the present invention and it may take for example the form of any of the cavities described in the patents referred to in the background of the present invention, above. Typically the cavity 14 is formed by sealing a periphery of substantially fluid impervious membrane or pad to the surface of the structure 12. Accordingly, a portion of the surface of the structure 12 forms a part of an internal surface of the cavity 14. The cavity 14 should be substantially sealed although it is recognized that due to the inherent permeability of various materials and imperfections in manufacturing processes and/or application of the cavity 14 to the structure 12, the cavity 14 may not be absolutely perfectly sealed.

The apparatus 10 comprises an unregulated pressure source 16 which is coupled to the cavity 14 via a fluid flow restriction 17. The pressure source 16 may take many different forms. In the illustrated embodiment in FIG. 1, the pressure source 16 comprises a pump 18 coupled to a vessel 20. In this particular embodiment the pump 18 is operated for a period of time to evacuate or pressurise the vessel 20 relative to atmosphere. The absolute pressure level within the vessel 20 is not critical and is not regulated. However a pressure in the order of 15-20 kpa above or below atmospheric pressure has been found suitable in preliminary testing. The pressure source 16 may provide fluid at a pressure above or below ambient pressure. That is, in its broadest and most general form the words "pressure source" are intended to cover both negative pressure (i.e. a vacuum) and positive pressure relative to ambient pressure.

In an alternate form, the pressure source 16 may comprise the pump 18 by itself and connected directly to the fluid flow restriction 17 rather than via an intervening vessel 20. In such an embodiment the pump 18 is operated as and when required to generate a non regulated pressure again typically in the order of ±15 to 20 kpa relative to ambient pressure.

In yet a further variation, the pressure source may simply comprise a body of fluid at a pressure different to the pressure of the atmosphere to which the cavity 14 is subjected. An example of this variation would be where the apparatus 10 is used in an aircraft with the cavity 14 subjected to the pressurised conditions within an aircraft flying at altitude, while the source is simply the atmospheric pressure external to the aircraft. In such an instance the pressure source is a relative negative pressure (i.e. a relative vacuum).

The fluid flow restrictor 17 has an effective fluid flow resistance r. However the fluid flow restrictor 17 need not be a single fluid flow resistance but rather may comprise a fluid flow restrictor circuit having a plurality of series and/or parallel connected fluid flow resistances. Indeed in such a circuit a switching arrangement may also be provided to allow easy switching in and out of individual fluid flow resistances to vary the overall effective fluid flow resistance r between the source 16 and the cavity 14. The fluid flow restrictor 17 may take many different forms including a high impendence tube, sintered glass, or a micro machine to channel or orifice and/or orifice plates.

The apparatus 10 further comprises a measurement system 19 that provides a measurement of, or related to, the volumetric airflow through the fluid flow restriction 17. More particularly, in the illustrated embodiment, the measurement system 19 comprises a first pressure transducer 22 coupled between the unregulated source 16 and the fluid flow restrictor 17; and a second pressure transducer 24 that is coupled between the cavity 14 and the fluid flow restrictor 17. The pressure transducer 22 provides a measure of the pressure P1 of the source 16 while the pressure transducer 22 provides a measure of pressure P2 of the cavity 14. As explained in greater detail below, the measurements provided by the transducers 22 and 24 (i.e. the measurement system 19) is related to the volumetric airflow through the restrictor 17.

If it is assumed that the only source of air leaking into or out of the apparatus 10 (depending on whether the pressure source is a relative negative or positive pressure) is via the cavity 14, then, in the event an air leak, there will be a flow of air F across the restrictor 17. A measure of conductivity to air flow of the cavity 14, termed the conductivity index CI, can then be calculated, typically by an on-board processor 21 that may form part of the measurement system 19 or is otherwise incorporated in the apparatus 10. When a crack 26 extends into the cavity 14, the conductivity index CI provides a measure of the conductance to air flow of the crack 26. The conductivity index is calculated as follows. The calculation is based on a hypothesis that for laminar (i.e. non-turbulent flow) the pressure drop across a flow restrictor is proportional to the magnitude of the resistance of the flow restrictor and the volumetric flow there through. This is described by the following equation:

$$\Delta P = r_{FR} \times \dot{V} \quad (1)$$

Where:

$\Delta P$ is the differential pressure in Pascals across the flow restrictor 17 [Pa]

$r_{FR}$ is the flow resistance of the flow restrictor in pascal-seconds per cubic meter [Pa·s/m$^3$]

$\dot{V}$ is the volumetric flow in meters cubed per second [m$^3$/s]

It is assumed that when the system is in equilibrium the mass flow through the cavity 14 and/or crack 26 is the same as the mass flow through the flow restrictor 17. Therefore a determination of the mass flow through the cavity 14/crack 26 can be made by calculating the mass flow through the flow restrictor 17. Mass flow is calculated from the volumetric flow and the gas density at the point of interest using equation (2). Because the point of interest is nominally at the centre of the restriction 17 the average of the end pressures is used in the density calculations as shown in equation (3).

$$\dot{m} = \rho \times \dot{V} \quad (2)$$

$$\begin{aligned}\dot{m}_{CRACK} &= \dot{m}_{FR} \quad (3)\\ &= \rho_{FR} \dot{V}_{FR} \\ &= \frac{P_{FR}}{RT} \times \frac{\Delta P_{FR}}{r_{FR}} \\ &= \frac{\frac{P_1 + P_2}{2}}{RT} \times \frac{P_2 - P_1}{r_{FR}}\end{aligned}$$

Where:

$\dot{m}$ is the mass flow in kilograms per second [kg/s]

$\rho$ is the gas density in kilograms per cubic meter [kg/m$^3$]

$P_{FR}$, $P_1$, $P_2$ is the pressure in Pascals [Pa] at: the centre of the restriction 17; the source 16; and the cavity 14, respectively R is the gas constant for dry air in joules per kilogram per Kelvin [J/Kg·K]

T is the temperature in kelvin [K]

Now that the mass flow through the cavity 14/crack 26 is known and the pressure difference across the crack is either measured or approximated using a standard ambient pressure the volumetric flow through the crack can be calculated using equation (2).

$$\dot{V}_{CRACK} = \frac{\dot{m}_{CRACK}}{\rho_{CRACK}} = \frac{\frac{P_1 + P_2}{2}}{RT} \times \frac{P_2 - P_1}{r_{FR}} \times \frac{1}{\frac{P_{CRACK}}{RT}}$$

Cancelling RT and expanding $P_{CRACK}$ leaves:

$$= \frac{P_1 + P_2}{2} \times \frac{P_2 - P_1}{r_{FR}} \times \frac{1}{\frac{P_3 + P_2}{2}}$$

$$= \frac{(P_1 + P_2)(P_2 - P_1)}{r_{FR}(P_3 + P_2)}$$

Using equation (1):

$$r_{CRACK} = \frac{\Delta P_{CRACK}}{\dot{V}_{CRACK}} = \frac{P_3 - P_2}{\frac{(P_1 + P_2)(P_2 - P_1)}{r_{FR}(P_3 + P_2)}}$$

$$= \frac{r_{FR}(P_3 + P_2)(P_3 - P_2)}{(P_1 + P_2)(P_2 - P_1)}$$

$$= \frac{r_{FR}(P_3^2 - P_2^2)}{P_2^2 - P_1^2}$$

Finally, as conductance is simply the inverse of resistance to flow the conductivity index CI can be calculated:

$$CI = \frac{1}{r} \quad (4)$$

$$\therefore CI_{CRACK} = \frac{1}{r_{CRACK}} = \frac{P_2^2 - P_1^2}{r_{FR}(P_3^2 - P_2^2)}$$

Where $P_3$ is the ambient pressure.

As mentioned above the calculation of the conductivity index CI, requires either a measure of ambient pressure $P_3$ or an assumption of a standard ambient pressure $P_3$. To this end, the apparatus 10 may further comprises an on board sensor or transducer to provide a measure of ambient pressure $P_3$. However in many applications, the ambient pressure $P_3$ may be assumed to be a constant 101325 Pa. In such instances, in the apparatus 10 the ambient pressure sensor can either be disabled or its reading simply discarded for the purposes of calculating the conductivity index. As the flow resistance r is known the product of the flow resistance r and the square of the ambient pressure in equation (4) above becomes a constant in the calculation of the conductivity index CI if a standard rather than measure ambient pressure $P_3$ is used.

When the apparatus 10 is connected to the cavity 14, if the cavity 14 is absolutely perfectly sealed the conductivity index CI provided by the apparatus 10 will be zero since $P_1$ will be the same as $P_2$. This indicates that there is no leakage of air through (i.e. into or out of) the cavity 14.

In the event that cavity 14 is not absolutely perfectly sealed then there will be some air flow through the cavity 14 and thus when the apparatus 10 is coupled with the cavity 14 the apparatus 10 will give a non-zero reading of conductivity index. That reading may be stored in a memory device associated with the processor 21 and is assigned to the particular cavity 14, or alternatively the reading may be held on a memory device that is retained with the cavity 14, for example on a socket that facilitates connection between the apparatus 10 and the cavity 14 where the socket is retained with the cavity 14.

If a crack 26 were to develop on the surface of a structure 12 and that crack extends into the cavity 14 to provide fluid communication between the cavity 14 and the surrounding atmosphere, there will be a flow F of air through the fluid flow restrictor 17 and thus, the apparatus 10 when connected with the cavity 14 will also provide a non-zero conductivity index.

The value of the conductivity index provides an indication of and is proportional to the volume of air flow through the cavity 14. Thus a higher conductivity index indicates the existence of a larger crack 26. Again, the conductivity index for the particular cavity 14 can be stored either on the apparatus 10 or on a memory device associated with the cavity 14. Once a measure of the conductivity index has been made, the apparatus 10 can be disconnected from the cavity 14.

At some later time the apparatus 10 may be reconnected with the cavity 14 to obtain a further reading of conductivity index. Any increase in measured conductivity index at the later time would be indicative of either a fresh crack 26 developing in the structure 12 that extends into the cavity 14 or alternatively an increase in the size of a crack 26 previously detected in the surface of the structure 12.

It is envisaged that the fluid flow restrictor 17 will have a flow resistance r in the range of between 500-2500 GPa·s/m³. Indeed, as previously suggested restrictor 17 may be in the form of a circuit comprising a plurality of series and/or parallel connected flow resistances of the same or different resistance together with a switch or other mechanism to effectively connect different flow resistances into the fluid circuit to provide a selection of overall flow resistance r. Increase in the resistance provides greater sensitivity or accuracy in the measurement of the conductivity index. This enables the detection of smaller or finer cracks. Switching in different flow restrictors of higher resistance will in effect provide a conductivity index having a greater degree of accuracy or number of decimal points.

The apparatus 10 may further comprise a bypass valve 28 connected in parallel across the flow restrictor 17 via a conduit 30. When the valve 28 is shut or closed (i.e. in an OFF state) the conduit 30 is blocked or sealed so that fluid communication between the source 16 and the cavity 14 is via the flow restrictor 17. This is the normal or measuring state where the apparatus 10 is used to provide a measure of the conductivity index of a cavity 14 and/or crack 26. It will be appreciated however that when the apparatus 10 is initially connected to the cavity 14 the cavity 14, being opened to the atmosphere, will contain a volume of air. Prior to the apparatus 10 being used to make a measure of the conductivity index, the air within the cavity 14 and any connection tube extending there from must be evacuated. This represents a "settling time" of the apparatus 10. It is preferable to have the settling time as short as possible so that measurements can be made quickly. By opening the valve 28 which is equivalent to the valve 28 being in an ON state, the flow restrictor 17 is effectively short circuited or bypassed and the cavity 14 is placed in communication with the source 16 via the conduit 30.

A continuity valve 32 may also be placed in communication with the cavity 14 on a side opposite the flow restrictor 17 by a further conduit 34. The continuity valve 32 can be used to confirm continuity in the communication path between the cavity 14 and the source 16. When the apparatus 10 is being used to make a measure of conductivity index, the continuity valve 22 is ordinarily in a closed or OFF state. In this way, the continuity valve 32 has no effect on the measure of conductivity index. However if the continuity valve 32 is briefly open, the cavity 14 will be vented to atmospheric pressure and one would therefore expect that the apparatus 10 would show a sharp or spiked change in conductivity index. If this has not occurred, it is assumed that there is a blockage between the cavity 14 and the source 16.

Now that an embodiment of the invention has been described in detail it will be apparent to those skilled in the relevant arts that numerous modifications and variations may be made without departing from the basic inventive concepts. For example the apparatus 10 has been described in relation to providing a measure of conductivity of a cavity or crack. It would be recognized by those skilled in the art that the apparatus 10 can be applied to provide a measure of permeability of a porous material such as concrete. In such an application the "cavity" can be formed as a surface cavity or as an internal cavity in the bulk of a concrete slab or core. Examples of such arrangements are shown in Applicant's U.S. Pat. No. 6,591,661, the contents of which is incorporated herein by way of reference. In a further modification, the measurement system may further comprise a differential pressure measurement device that is connected in parallel to and across the flow restrictor 17 to provide a pressure differential $P_4=P_2-P_1$. This pressure sensor may have "course" and "fine" measurement scaling such that a small pressure difference (indicative of a very small crack 26) can be measured with greater resolution and accuracy. As previously mentioned the pressure source 16 may be a relative vacuum or a positive pressure relative to ambient pressure. All modifications and variations that would be obvious to a person of ordinary skill in the art are deemed to be within the scope of the present invention the nature of which is to be determined from the above description and the appended claims.

The invention claimed is:

1. An apparatus for measuring the conductivity to air flow of a sealed cavity formed on a surface of a structure or a component where a portion of the surface forms part of an internal surface of the cavity, the apparatus comprising:
   an unregulated pressure source;
   a fluid flow restrictor having a flow resistance r and providing fluid flow communication between the cavity and the pressure source;
   a measurement system for: providing a measurement of, or related to, the volumetric air flow through the flow restriction; and calculating a conductivity index CI to air flow of the cavity in accordance with the equation CI=flow/pressure difference
   where "flow" is the volumetric flow of air through the fluid flow restriction measured by the measurement system; and "pressure difference" is the difference in pressure across the cavity with reference to atmospheric or ambient pressure.

2. The apparatus according to claim 1 further comprising a continuity valve coupled to an end of the cavity opposite the fluid flow restrictor, the continuity valve having a ON state in which the valve is open and vents the cavity to atmospheric pressure, and an OFF state in which the continuity valve is shut.

3. The apparatus according to claim 1 further comprising a bypass valve connected in parallel across the fluid flow restrictor to provide direct fluid communication between the unregulated pressure source and the sealed cavity when the bypass valve is in an ON state.

4. The apparatus according to claim 1 wherein a standard or fixed ambient pressure is provided to the measurement system for calculation of the conductivity index.

5. The apparatus according to claim 1 wherein the measurement system comprises a memory for storing the conductivity index of a crack.

6. The apparatus according to claim 5 wherein the apparatus is configured to compare a stored conductive index with a calculated conductivity index for the same crack to subsequently provide an indication of rate of growth of the crack.

7. The apparatus according to claim 1 wherein the measurement system comprises a first pressure transducer providing a measure of pressure P1 of the unregulated pressure source; and, a second pressure transducer providing a measure of pressure P2 on a side of the cavity connected with the fluid flow restrictor.

8. The apparatus according to claim 7 further comprising an ambient pressure sensor or transducer for providing a measure of ambient pressure P3 and the measurement system includes the measure of ambient pressure in the calculation of the conductivity index.

9. The apparatus according to claim 8 wherein the conductivity index is calculated by the measurement system using the equation:

$$CI = \frac{P_2^2 - P_1^2}{r_{FR}(P_3^2 - P_2^2)}$$

where:
   $P_1$=the pressure in Pascals of the source
   $P_2$=the pressure in Pascals on a side of the fluid flow restriction distant the source
   $P_3$=ambient pressure in Pascals, either measured or nominal
   $r_{FR}$=the flow resistance of the restriction in Pascal seconds per meter cubed.

10. An apparatus for measuring the conductivity to air flow of a crack on a surface of a structure, the surface having applied to it an impervious member forming a sealed cavity that is breached by the crack in the surface, the apparatus comprising:
   an unregulated pressure source;
   a fluid flow restrictor having a flow restrictor r and providing fluid communication between the cavity and the pressure source;
   a measurement system for: providing a measurement of, or related to, the volumetric air flow through the flow restriction; and calculating a conductivity index CI of air flow through the crack on the basis of the flow resistance r and the measurement of volumetric air flow.

11. The apparatus according to claim 10 further comprising a continuity valve coupled to an end of the cavity opposite the fluid flow restrictor, the continuity valve having a ON state in which the valve is open and vents the cavity to atmospheric pressure, and an OFF state in which the continuity valve is shut.

12. The apparatus according to claim 10 further comprising a bypass valve connected in parallel across the fluid flow restrictor to provide direct fluid communication between the unregulated pressure source and the sealed cavity when the bypass valve is in an ON state.

13. The apparatus according to claim 10 wherein a standard or fixed ambient pressure is provided to the measurement system for calculation of the conductivity index.

14. The apparatus according to claim 10 wherein the measurement system comprises a memory for storing the conductivity index of a crack.

15. The apparatus according to claim 14 wherein the apparatus is configured to compare a stored conductive index with a calculated conductivity index for the same crack to subsequently provide an indication of rate of growth of the crack.

16. The apparatus according to claim 10 wherein the measurement system comprises a first pressure transducer providing a measure of pressure P1 of the unregulated pressure source; and, a second pressure transducer providing a measure of pressure P2 on a side of the cavity connected with the fluid flow restrictor.

17. The apparatus according to claim 16 further comprising an ambient pressure sensor or transducer for providing a measure of ambient pressure P3 and the measurement system includes the measure of ambient pressure in the calculation of the conductivity index.

18. The apparatus according to claim 17 wherein the conductivity index is calculated by the measurement system using the equation:

$$CI = \frac{P_2^2 - P_1^2}{r_{FR}(P_3^2 - P_2^2)}$$

where:
- $P_1$=the pressure in Pascals of the source
- $P_2$=the pressure in Pascals on a side of the fluid flow restriction distant the source
- $P_3$=ambient pressure in Pascals, either measured or nominal
- $r_{FR}$=the flow resistance of the restriction in Pascal seconds per meter cubed.

19. A method of condition monitoring of a component or a structure comprising:
- forming a substantially sealed cavity on or in the component or structure;
- connecting an unregulated vacuum source via a fluid flow restriction to the cavity, where the restriction has a flow resistance r;
- providing an indication of air flow into the cavity based on a measured volumetric air flow through the restriction and a measured pressure difference across the cavity.

20. An apparatus for condition monitoring of a component or structure comprising:
- a sealed cavity on or within the component or structure;
- an unregulated pressure source;
- a fluid flow restriction having a flow resistance r and providing fluid communication between the cavity and the source;
- a measurement system for: providing a measurement of, or related to, the volumetric air flow through the flow restriction; and, providing an indication of a conductivity index to air flow of the cavity based on the flow resistance r and the measurement of or related to the volumetric air flow.

* * * * *